US009741114B2

(12) United States Patent
Varkuti

(10) Patent No.: US 9,741,114 B2
(45) Date of Patent: Aug. 22, 2017

(54) QUANTIFICATION OF BRAIN VULNERABILITY

(71) Applicant: Brainlab AG, Munich (DE)

(72) Inventor: Bálint Varkuti, Munich (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/034,077

(22) PCT Filed: Nov. 5, 2013

(86) PCT No.: PCT/EP2013/073042
§ 371 (c)(1),
(2) Date: May 3, 2016

(87) PCT Pub. No.: WO2015/067299
PCT Pub. Date: May 14, 2015

(65) Prior Publication Data
US 2016/0284082 A1    Sep. 29, 2016

(51) Int. Cl.
*G06K 9/00* (2006.01)
*G06T 7/00* (2017.01)
(Continued)

(52) U.S. Cl.
CPC ............ *G06T 7/0012* (2013.01); *A61B 5/055* (2013.01); *A61B 5/4064* (2013.01); *A61B 6/032* (2013.01);
(Continued)

(58) Field of Classification Search
CPC .............. G06T 7/00; A61B 5/00; G06F 19/00
(Continued)

(56) References Cited

U.S. PATENT DOCUMENTS 6,366,797 B1 * 4/2002 Fisher ................... A61B 5/055
128/922
2010/0260396 A1 * 10/2010 Brandt ................. G06K 9/4671
382/131

FOREIGN PATENT DOCUMENTS

| WO | 2011025836 | 3/2011 |
| WO | 2011128823 | 10/2011 |
| WO | 2012092511 | 7/2012 |

OTHER PUBLICATIONS

Achard S, et al. (2006): A resilient, lowfrequency, small-world human brain functional network with highly connected association cortical hubs. The Journal of Neuroscience: The Official Journal of the Society for Neuroscience 26 (1):63-72 Jan. 1, 2006.
(Continued)

*Primary Examiner* — Abolfazl Tabatabai
(74) *Attorney, Agent, or Firm* — Middleton Reutlinger

(57) ABSTRACT

The invention relates to a medical data processing method for determining a vulnerability field of a brain of a patient, the steps of the method being constituted to be executed by a computer and comprising: a) acquiring a nerve-indicating dataset comprising information about the brain of the patient suitable for identifying neural fibers in the brain of the patient; b) determining nodes within the brain preferably being neuron-rich grey matter parts of the brain; c) determining the axonal linkage of the nodes based on the nerve-indicating dataset to obtain edges connecting the nodes, the nodes and edges constituting a connectivity graph; d) determining a weight for each of the edges depending on centrality graph theoretical statistical measure of the respective edge in the connectivity graph; e) determining, for each of the edges, which voxels in a dataset of the brain of the patient belong to the edges or are passed by the edges and assigning or adding the determined weight of the respective edges to all of the voxels belonging to the respective edge to
(Continued)

obtain a weighted voxel-based dataset of the brain of the patient defining the vulnerability field of the brain.

16 Claims, 6 Drawing Sheets

(51) Int. Cl.
| | |
|---|---|
| *G06T 17/00* | (2006.01) |
| *A61B 6/03* | (2006.01) |
| *A61B 5/055* | (2006.01) |
| *A61B 5/00* | (2006.01) |
| *A61B 8/08* | (2006.01) |
| *G06F 17/16* | (2006.01) |
| *A61B 5/04* | (2006.01) |
| *G06F 19/00* | (2011.01) |
| *A61B 6/00* | (2006.01) |

(52) U.S. Cl.
CPC .............. *A61B 6/037* (2013.01); *A61B 6/501* (2013.01); *A61B 8/0808* (2013.01); *A61B 8/488* (2013.01); *G06F 17/16* (2013.01); *G06F 19/3437* (2013.01); *G06T 17/005* (2013.01); *A61B 6/481* (2013.01); *G06F 19/321* (2013.01); *G06T 2207/10081* (2013.01); *G06T 2207/10088* (2013.01); *G06T 2207/10092* (2013.01); *G06T 2207/10104* (2013.01); *G06T 2207/30016* (2013.01); *G06T 2207/30241* (2013.01); *G06T 2210/41* (2013.01)

(58) Field of Classification Search
USPC ....... 382/128, 129, 130, 131, 132, 133, 134; 600/25, 378, 544
See application file for complete search history.

(56) References Cited

OTHER PUBLICATIONS

Bassett DS, et al. (2011): Conserved and variable architecture of human white matter connectivity, NeuroImage 54 (2):1262-79 Jan. 1, 2011.

Gigandet X, et al. Estimating the confidence level of white matter connections obtained with MRI tractography. PloS one 3(12):e4006 Jan. 1, 2008.

Gong G, et al. (2009), Mapping anatomical connectivity patterns of human cerebral cortex using in vivo diffusion tensor imaging tractography. Cerebral cortex (New York, N.Y.: 1991) 19(3):524-36 Jan. 1, 2009.

Hagmann P, et al. (2007): Mapping human whole-brain structural networks with diffusion MRI. PloS one 2(7):e597 Jan. 1, 2007.

Iturria-Medina Y, et al. (2008): Studying the human brain anatomical network via diffusion-weighted MRI and Graph Theory. NeuroImage 40(3):1064-76 Jan. 1, 2008.

Kreher BW, et al. (2008): Connecting and merging fibres: pathway extraction by combining probability maps. NeuroImage 43(1):81-9 Jan. 1, 2008.

Rubinov M, et al. (2009): Complex network measures of brain connectivity: uses and interpretation. NeuroImage 52(3): 1059-1069. Jan. 1, 2009.

Spoms O, et al. (2005): The human connectome: A structural description of the human brain. PLoS computational biology 1(4):e42 Jan. 1, 2005.

van den Heuvel MP (2009): Functionally linked resting-state networks reflect the underlying structural connectivity architecture of the human brain. Human brain mapping 30(10):3127-41 Jan. 1, 2009.

Varkuti B, (2011): Quantifying the link between anatomical connectivity, gray matter volume and regional cerebral blood flow: an integrative MRI study. PloS one 6(4):e14801 Jan. 1, 2011.

Zalesky A, et al. (2010): Whole-brain anatomical networks: does the choice of nodes matter? NeuroImage 50 (3):970-83 Jan. 1, 2010.

Mori S, et al. (2008): Stereotaxic white matter atlas based on diffusion tensor imaging in an ICBM template. Neuroimage 40(2): 570-582. Jan. 1, 2008.

European Patent Office, International Search Report and Written Opinion of PCT/EP2013/073042 May 16, 2014.

Calamante et al., Track-weighted functional connectivity (TW-FC): A tool for characterizing the structural-functional connections in the brain, Neuroimage, vol. 70 Jan. 5, 2013.

Margulies et al., Visualizing the human connectome, Neuroimage, vol. 80 May 6, 2013.

Sporns, Structure and function of complex brain networks, Dialogues in Clinical Neuroscience, vol. 15 Sep. 30, 2013.

Fornito et al. Graph analysis of the human connectome: Promise, progress, and pitfalls, Neuroimage, vol. 80 Apr. 30, 2013.

\* cited by examiner

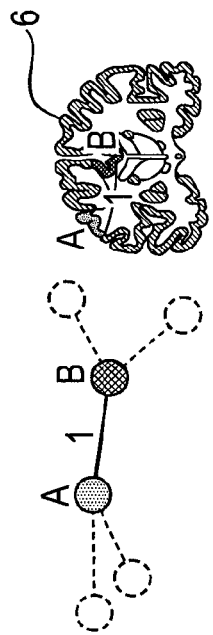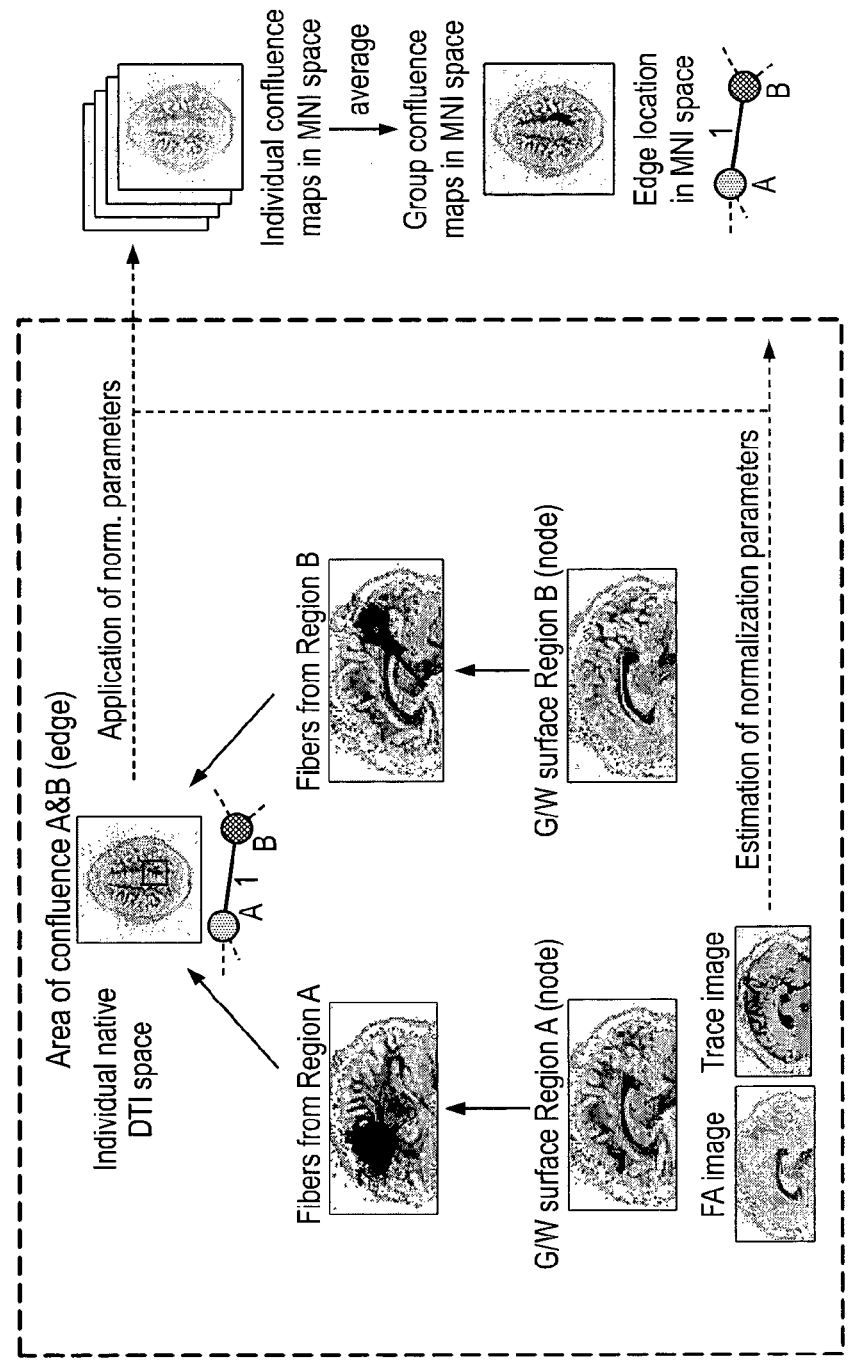

QUANTIFICATION OF BRAIN VULNERABILITY

The present invention relates to a data processing method for determining a vulnerability field of a brain of a patient, a computer program, a computer and a medical diagnostic system. A more specific aspect is directed to a data processing method for the image-based voxel-by-voxel quantification of brain vulnerability for optimal surgical or radiation therapy trajectory planning Planning any neurosurgical or radiation trajectory towards an anatomical or functional target in the brain is currently done in a stepwise procedure. In the case of neurosurgery, first the access is chosen based on known best surgical practice (e.g. standard craniotomy accesses such as pterional, subtemporal, anterior parasagittal, posterior parasagittal, median suboccipital, or lateral suboccipital) or by utilizing planning software that visualizes the position of the target in relation to other brain structures (this is used for radiation therapy planning to avoid high radiation dosage to risk structures).

The procedure of individualized planning is usually based on CT or MR images of the patient that are loaded into a visualization or planning software environment and/or on standard atlas images.

WO 2012/159671 A1 discloses a method for generating planning data or control data for a radiation treatment.

EP 0 945 814 A2 discloses a method and system for providing artificial intelligence for planning and risk assessment of surgical paths.

EP 0 945 815 A2 discloses a method and system for assessing risks and prognosis of a given cause of medical treatment.

EP 1 844 725 A1 discloses risk assessment for planned trajectories.

US 2009/025923 A1 discloses a method and an apparatus for optimal trajectory planning U.S. Pat. No. 8,249,892 B2 discloses a method of data mining in medical applications.

WO 2011/128823 A2 discloses a system and method for planning a neurosurgical operation.

US 2011/0245625 A1 discloses path planning for reducing tissue damage in minimally invasive surgery.

U.S. Pat. No. 8,238,520 B2 discloses treatment plan optimization methods for radiotherapy.

U.S. Pat. No. 8,060,181 B2 discloses risk assessment for planned trajectories.

The following publications are concerned with the field of the present inventions and are also cited in this application:

Achard S, Salvador R, Whitcher B, Suckling J, and Bullmore E (2006): A resilient, low-frequency, small-world human brain functional network with highly connected association cortical hubs. The Journal of Neuroscience: The Official Journal of the Society for Neuroscience 26(1):63-72

Bassett D S, Brown Ja, Deshpande V, Carlson J M, and Grafton S T (2011): Conserved and variable architecture of human white matter connectivity. NeuroImage 54(2):1262-79

Gigandet X, Hagmann P, Kurant M, Cammoun L, Meuli R, and THiran J P (2008): Estimating the confidence level of white matter connections obtained with MRI tractography. PloS one 3(12):e4006

Gong G, He Y, Concha L, Lebel C, Gross D W, Evans A C, and Beaulieu C (2009a): Mapping anatomical connectivity patterns of human cerebral cortex using in vivo diffusion tensor imaging tractography. Cerebral cortex (New York, N.Y.: 1991) 19(3):524-36

Hagmann P, Kurant M, Gigandet X, Thiran P, Wedeen V J, Meuli R, and Thiran J P (2007): Mapping human whole-brain structural networks with diffusion MRI. PloS one 2(7):e597

Iturria-Medina Y, Sotero R C, Canales-Rodríguez E J, Alemán-Gómez Y, and Melie-García L (2008): Studying the human brain anatomical network via diffusion-weighted MRI and Graph Theory. NeuroImage 40(3):1064-76

Kreher B W, Schnell S, Mader I, Il'yasov Ka, Hennig J, Kiselev V G, and Saur D (2008): Connecting and merging fibres: pathway extraction by combining probability maps. NeuroImage 43(1):81-9

Rubinov M and Sporns O (2009): Complex network measures of brain connectivity: uses and interpretation. NeuroImage 52(3): 1059-1069.

Sporns O, Tononi G, and Kotter R (2005): The human connectome: A structural description of the human brain. PLoS computational biology 1(4):e42 van den Heuvel M P, Mandl R C W, Kahn R S, and Hulshoff Pol H E (2009): Functionally linked resting-state networks reflect the underlying structural connectivity architecture of the human brain. Human brain mapping 30(10): 3127-41

Várkuti B, Cavosoglu M, Kullik A, Schiffler B, Veit R, Yilmaz O, Rosenstiel W, Braun C, Uludag K, Birbaumer N, and Sitaram R (2011): Quantifying the link between anatomical connectivity, gray matter volume and regional cerebral blood flow: an integrative MRI study. PloS one 6(4): e14801

Zalesky A, Fornito A, Harding I H, Cocchi L, Yücel M, Pantelis C, and Bullmore E T (2010): Whole-brain anatomical networks: does the choice of nodes matter? NeuroImage 50(3):970-83

Mori S, Kenichi O, Hangyi J, Li J, Xin L, Kazi A, Kegang H et al. (2008) Stereotaxic white matter atlas based on diffusion tensor imaging in an ICBM template. Neuroimage 40(2): 570-582.

It is a problem to be solved by the present invention to provide an improved data processing method for determining a vulnerability field of a brain of a patient, as well as a corresponding computer program, computer and a medical system. This is achieved by the subject-matter of the independent claims. Advantageous embodiments are defined in the dependent claims.

EXEMPLARY SHORT DESCRIPTION OF THE INVENTION

In the following, a short description of specific features of the present invention is given which shall not be understood to limit the invention only to the features and combinations of features described in this section.

The invention provides in particular a method of determining a vulnerability field of a patient's brain which comprises the following features: A nerve indicating data set is acquired for example on the basis of diffusion tensor imaging data and neural fibres in the brain are determined as of edges between nodes representing neuron-rich grey brain matter parts. A weight is assigned to each of the edges based on graph theoretical properties, in particular a graph theoretical statistical measure such as centrality or vulnerability, of the edge, and it is further determined which voxels are traversed by a specific edge, and the weight of that edge is assigned to each one of the traversed voxels. On the basis of a thus-obtained map of weighted voxels, a vulnerability field representing a vulnerability map of the brain with regard to specific risks associated with a medical procedure can be generated.

The vulnerability map can also be generated based on multiple sets of image data each generated with a different medical imaging modality. This allows to include information relating to different types of risk depending on the type of tissue which can sensibly be imaged with the respective medical imaging modality.

An optimum trajectory between an entry point on the surface of the patient's body (e.g. the outer surface of the skull) and a target region which is to be treated by an envisaged medical procedure (e.g. brain surgery or radiation therapy) can be determined such that risk regions are avoided by the trajectory based on the vulnerability map.

GENERAL DESCRIPTION OF THE INVENTION

In this section, a description of the general, in particular preferred, features of the present invention is given.

In order to solve the aforementioned problem, a data processing method (in particular a medical data processing method, i.e. a data processing for use in connection with a medical procedure such as surgery or radiotherapy) for determining a vulnerability field of a brain of a patient, which can be human or an animal, includes one or more of the following preferable steps preferably being constituted to be executed by a computer (in particular are executed by a computer):

a) Acquiring a Nerve-Indicating Dataset Comprising Information About the Brain of the Patient Suitable for Identifying Neural Fibres in the Brain of the Patient This method uses individual patient images as input (and potentially population/sample based atlas images), processes these, allows the user to attune the weightings of the specific vulnerability fields if necessary and produces a combined vulnerability field that can be utilized by cost functions to produce a ranked list of objectively optimal trajectories for a given target. Additionally the trajectories are annotated with estimations on the disruptive effect each trajectory might have on brain function.

In order to allow for an inverse trajectory planning which starts at the surgical/radiation target in question a vulnerability field has to be generated from the available patient-specific imaging data. If for certain types of information (depending in particular on the imaging modality which was used to generate the images which serve as a basis for the nerve-indicating dataset) patient-specific imaging data is not available, it is possible to obtain population- or matched-sample based imaging data and bring that information into the patient-specific space.

Such a situation might arise if the field of view coverage of the dataset indicating the fibre, in particular the nerve, does not cover e.g. the entire brain and certain parts of the individual brain are therefore not imaged. In such a situation retrieving population- or matched-sample based information to complement or interpolate the missing information required to accurately determine certain global properties is preferred over not having access to any information from the not imaged anatomical areas at all.

Furthermore it is possible to use patient-specific imaging data acquired at earlier points in time in order to update the vulnerability field based access/trajectory planning at later points in time. Such a situation might arise if e.g. in an intraoperative setting MR imaging for the generation of a dataset indicating the fibre, in particular the nerve, is not available, but such information from preoperative imaging clusters can be used and is to be "updated" by e.g. means of elastic image fusion.

The available imaging data can be generated (in particular outside of the inventive method, in particular before the inventive method is executed) by any imaging modality, in particular it can be generated on the basis e.g. CT scans, angiography, T1-weighted MR imaging, T2-weighted MR imaging, Proton Density Imaging, forms of metabolism related imaging (with contrast material and without, using Positron Emission Tomography or perfusion imaging e.g. forms of Arterial Spin Labeling), Diffusion Tensor Imaging (DTI, in particular Diffusion Spectrum Imaging, q-Ball Imaging/HARDI), Magnetic Resonance Spectroscopy, functional Magnetic Resonance Imaging (fMRI) and many more. The imaging data serves as basis for generating the nerve-indicating dataset. For example, a DTI image dataset can be generated which depicts two crossing neural fibres. Diffusion tensors of the DTI are represented by circles and ellipses in such an image. The shape of the representation of a tensor indicates the directional distribution of the tensor, such as a Bingham distribution. In general, the directional distribution is three-dimensional. For a particular direction, the directional distribution provides the probability with which the neural fibre runs in this particular direction. Based on such information, information about a certain probability for neural fibres having the positions and orientations described by the DTI image can be determined and serve as a basis for generating the nerve indicating data, which describes in particular such positions and/or orientations. A technique of determining the probability is described for example in the applicants's patent application having the title "Localization of fibrous structures" and the PCT application number PCT/EP2012/065567, the entire contents of which herewith is incorporated into the present disclosure by reference.

In a typical case, the nerve-indicating dataset does not comprise a particular direction of the neural fibre at the current point, but rather a probability distribution of the neural fibres direction, such as a Bingham distribution. The direction of the path vector representing the path of a neural fibre is stochastically calculated based on the directional distribution. Preferably, the length of the path vector is also determined based on the directional distribution, for example being proportional to the inverse of the probability of the direction of the path vector. If the end point of the path vector lies within a constraining volume, then this end point is used as the new current point and a new path vector is calculated for this current point, such that the path is iteratively established. If the end point of the path vector lies on an end surface of the constraining volume other than the end surface on which the seat point of the path lies, then a valid path has been found. The endpoint of the path vector lying outside the constraining volume can have two different causes. In the first case, the path vector extends through an end surface other than the end surface comprising the seed point. In this case, a valid path has been found. In the second case, the path vector extends through any other surface of the constraining volume. In this case, a part of the path lies outside the constraining volume such that path determination is stopped and the path is discarded.

Via preprocessing algorithms (e.g. tissue segmentation, tensor estimation, regional Cerebral Blood Flow calculation etc.) the raw data is converted into information maps that contain information on the following exemplary (but not limited to) voxel-specific factors: present anatomical structure (nerve, vessel, fluid, brain tissue, bone etc.), tissue class probability (grey brain matter, white brain matter etc.) perfusion of that voxel (regional Cerebral Blood Flow in ml/100 gr/min), diffusivity of that voxel and presence/concentration of certain neurotransmitter types or metabolites (MRS/PET).

PET

For example, Positron Emission Tomography (PET) imaging of cerebral metabolism is utilized to determine baseline brain function abnormalities, both in the sense of hypometabolism syndromes (e.g. hypofrontality in certain forms of neurodegenerative disorders) as well as in the sense of determining zones of heightened activity, that have given cause for suspicion (e.g. PET-positive tumor tissue). PET images can be used to enhance the trajectory planning by defining the target zone more precisely and can generate metabolism based vulnerability maps, where zones of high/low metabolism are to be circumvented during trajectory planning T1-MR, Anatomical For example, T1-MR imaging is used, and the resulting imaging provides anatomical information that is used for segmentation. Tissue maps are generated from the segmentation process and the tissue types can enter the process as vulnerability fields. Grey matter is to be avoided to preserve neural tissue, white matter at certain key structures/bottlenecks (e.g. cerebellar pedunculi) is to be avoided and ventricles filled with cerebro-spinal fluid (CSF) can cause dramatic brain shift/CSF leakage when punctured, which can enter the planning process as a vulnerability information field of its own.

fMRI Time Series, Functional

For example, using fMRI analysis (block/event-related task/stimulation based or resting state) allows for the estimation of voxel-blocks that show a behaviour of functional cooperation in a given situation. These areas can be estimated e.g. from functional connectivity analysis of the time series. Such cooperative groups (e.g. in the case of a motor task the voxels in the M1 area of the patient's brain) show a BOLD activation/deactivation behaviour that allows their association with a certain trait (e.g. patients suffering from AD have an abnormality in the resting state functional connectivity network in the frontal brain area) or state (e.g. patients performing a bilateral motor task show activity in both M1 regions together with activity in the SMA of the brain). This network information is of highest clinical relevance, as the incorporation of such activity profiles into the trajectory planning process allows the surgeon/oncologist to circumnavigate such functional groups and to preserver healthy/residual brain function in certain (sub-)systems.

Angiogram Generating Imaging (CT, MR Based)

As another example, the nerve-indicating dataset may be generated from a CT- or MR-based angiogram.

The patient-specific generation of an angiogram is a classical vulnerability information field that requires little to no post-processing. Major vessels are to be avoided in any surgical procedure and restrict the zone of plausible craniotomy accesses on the skull surface.

pASL, ASL, Functional, Doppler Imaging

As further exemplary imaging methods, contrast-agent and isotope free methods for the estimation of cerebral perfusion in vivo, such as pASL, ASL and Doppler imaging, allow for the construction of partial or whole brain perfusion maps, containing estimates of the regional Cerebral Blood Flow, Blood Volume and other metrics (e.g. $CMRO_2$ level) in a given voxel. In any surgical intervention the surgeon wishes to minimize the blood loss occurring during the surgery and tries to avoid major vessel structures. Further areas of high resting-state or task-based perfusion are known to play a significant role in higher order functions such as consciousness and to consist of association cortex regions of high functional heterogeneity. Avoiding these important regions in the course of surgery is of natural importance, and therefore such a perfusion map can directly be used as a vulnerability map.

DTI, DSI, q-Ball, HARDI

As even further examples, DTI, DSI, q-Ball or HARDI may be used to generate the nerve-indicating dataset.

The most simple use of such an input is the calculation of scalar maps from the tensor information (classically Fractional Anisotropy, Apparent Diffusion Coefficient, Mean Diffusivity etc.). These scalar maps can further be used to be converted into vulnerability maps (e.g. high FA voxels carry usually well myelinated axon bundles and should be avoided). The information can further be fused with either predetermined seed points or with seed points determined specifically within the individual patient's images. The seed points (usually located on the grey brain matter surface) can be utilized to perform deterministic or probabilistic fibre tracking to reconstruct the major white matter tracts of the brain and to obtain information on the macroscopic connectivity pattern of the individual brain. Such information can be mined to back-project the physical location of an individual fibre bundle that connects a pair of grey matter zones. The disruption of such a fibre would cause direct disconnection of the zone pair and such disruption can be quantified in a vulnerability metric.

b) Determining Nodes Within the Brain Preferably Being Neuron-Rich Grey Matter Parts of the Brain In graph or complexity analysis of structural brain connectivity (van den Heuvel et al., 2009), anatomical images are generally used to parcellate neuron-rich grey matter (i.e. grey brain matter) parts of the brain by using a standard canonical brain atlas (Zalesky et al., 2010) into nodes, whose axonal linkage we seek to study by reconstructing the white matter fibre tracts directly, connecting one node to another, from the DTI data of the same subject.

Individual Connectome Reconstruction

The methods are described in detail in Várkuti et al. (2011) and Kreher et al. (2008). In order to define the network nodes, grey matter areas were labelled for each subject individually based on the AAL atlas, resulting in 116 nodes (80 cortical, 10 subcortical, 26 cerebellar) by using the procedure of normalization and parameter inversion to localize atlas region in DTI native space. Normalization and inverse transformation were implemented using the SPM8 package. Using in-house code, the white matter voxels, which were neighbouring the grey matter of each zone marked as network node, were defined as seed voxels of that area. Only voxels with a fractional anisotropy (FA) value above 0.3 (grey matter FA can reach values up to 0.2) were admitted to this procedure. In addition, these voxels also had to be labelled as white matter by the segmentation step and reside within the brain outline mask resulting from the iterative Brain Extraction Step.

c) Determining the Axonal Linkage of the Nodes Based on the Nerve-Indicating Dataset to Obtain Edges Connecting the Nodes, the Nodes and Edges Constituting a Connectivity Graph Although in network analysis parts of the brain are represented by edges and nodes of the graph (Gong et al., 2009a; Hagmann et al., 2007; Iturria-Medina et al., 2008), edge and node properties remain mere abstractions to describe the underlying graph in a more understandable and analyzable mathematical format until not back-projected into the real brain space and related to function.

The reality of an anatomical connectivity graph edge in the brain is a bundle of white matter fibres, which originate mostly on the grey/white matter surface of at least one brain region (node) and traverse the brain. As the bundle is stretching through the cerebral space it is being joined by other bundles from other origins as well as left by tracts branching away from the main bundle, only to finally arrive at its destination region and merge again into another grey/white matter surface. DTI does not allow us to obtain any information on whether we are studying ascending, descending or mixed fibres—the direction of information within a fibre—or the synaptic nature of the link—whether it is part of a polysynaptic link across many nodes or a monosynaptic direct link between a pair of nodes. Hence the adjacency matrix constituting the white matter network graph is usually an undirected description and in this simplification a fibre connects region A to B as much as B to A.

The white matter architecture of each individual is slightly different (Gigandet et al., 2008; Bassett et al., 2011) so that the bundles are curving in different ways connecting different pairs of regions. Interestingly in their totality and sum the entirety of these single tracts always elicit a similar macroscopic pattern of main bundles, that is described by the common white matter atlases (Mori et al., 2008). The zones described in these white matter atlases, such as for example the fasciculus longitudinalis (FL) or the corticospinal tract (CST), might not contain the exact same bundles or connections in every subject, but appear across subjects as macroscopically similar, in the sense that they are located at similar positions, have a similar main orientation of the white matter fibres (CST are always ascending/descending, FL tracts connect the brain along the anterior-posterior axis) and mostly carry a majority of connections with comparable functionality (e.g. association fibres). Each voxel within such a white matter zone is part of at least one white matter bundle that crosses through that voxel and this connection can be more or less important in terms of graph centrality. So although structural connectivity across brains may be variable to an extent, a large part of it—the connectome backbone so to speak—is shared and the graph edges of that common connectivity skeleton have shared properties. If that was not the case we would not show patterns of brain function and information processing that are comparable across members of the species.

As is generally known in the field of graph theory and network analysis, there are multiple metrics to describe graph properties of edges or a given vertex, for example a graph theoretical statistical measure can be used for such a description. Examples of such a graph theoretical measure are centrality and edge vulnerability. Centrality is a measure for describing the importance of a vertex (within this disclosure also called node) within a graph. The present invention preferably uses edge vulnerability for the estimation of one vulnerability field, however betweenness centrality or degree centrality may be used in an alternative, less preferred embodiment.

Edge vulnerability is a graph theoretical metric that measures the impact that removing a given edge in a graph would have on the paths connecting nodes in the graph. High-vulnerability edges are located at points of the graph that can be described as bottlenecks, here the overall system has low attack tolerance, since a local change (the removal of the edge) would have a massive impact on global properties of the graph such as e.g. average path length. The edge vulnerability metric describes how strongly the average shortest path lengths (the mean distance to get from any node A to any node B) in a network grow if the edge is removed.

In that sense the measure is closely related to local measures such as edge betweenness centrality and is strongly determined also by global properties of the graph such as global efficiency (the ratio of parallel connections/alternative routes of equal/comparable length connecting any two nodes).

In an undirected graph $G:=(V, E)$ with V vertices the edge vulnerability of an edge i could be computed as the difference between the average shortest path lengths with and without the edge in question.

1. For each pair of vertices (s,t), compute the shortest paths between them.
2. Determine the average path lengths of the graph G by dividing the sum of shortest paths for all pairs of vertices (s,t) through the number of vertice pairs.
3. Remove i from the graph G to produce $G_i$ and recalculate for each pair of vertices (s,t) the shortest paths between them.
4. Determine the average path lengths of the graph $G_i$ by dividing the sum of shortest paths for all pairs of vertices (s,t) through the number of vertice pairs.
5. Subtract the average shortest path length of G (step 2) from the average shortest path length of G (step 4), the larger the resulting number the higher is the vulnerability of edge i Betweennes centrality is a centrality measure of a vertex within a graph. Betweenness centrality quantifies the number of times a node acts as a bridge along the shortest path between two other nodes. Thus, betweenness centrality can be regarded as a measure for the importance of that specific node for a connection between the other two nodes. In particular, betweenness centrality can be understood as a measure for the probability that there is another path between the other two nodes which does not cross the specific node, i.e. that there is an alternative route between the two nodes which does not cross the specific node. The betweenness centrality of a vertex v in a graph $G:=(V, E)$ with V vertices is computed as follows:

1. For each pair of vertices (s,t), compute the shortest paths between them.
2. For each pair of vertices (s,t), determine the fraction of shortest paths that pass through the vertex in question (here, vertex v).
3. Sum this fraction over all pairs of vertices (s,t).

The betweenness centrality $C_B(v)$ can therefore be written as $$C_B(v) = \sum_{s \neq v \neq t \in V} \frac{\sigma_{st}(v)}{\sigma_{st}}$$

where $\sigma_{st}$ is the total number of shortest paths from node s to node t and $\sigma_{st}(v)$ is the number of those paths that pass through v. The betweenness may be normalised by dividing through the number of pairs of vertices not including v, which for directed graphs is $(n-1)(n-2)$ and for undirected graphs is $(n-1)(n-2)/2$.

Degree centrality is defined as the number of links which are incident upon a node (i.e. the number of ties that a node has). The degree centrality $C_D(v)$ of a vertex v for a given graph $G:=(V, E)$ with $|V|$ vertices and $|E|$ edges is defined as $C_D(v)=\deg(v)$.

For estimation of the white matter fibres probabilistic tracking from the node/vertex-specific seed points can be realized by using e.g. the PiCo approach. The number of random walks can be adjusted to the number of voxels within the white matter tracking area for each single seed point. The algorithms implemented in the DTI and Fibretools Software Package (Kreher et al., 2008) allow for creating extended visitation maps for the tracking from each seed set (all seed voxels of an AAL area) separately, based on the curves originating from the seed points and being propagated through the tensor field (number of curves equalling the number of random walks) and combine this information with statistical estimates on the plausibility of confluence of two white matter tracts anywhere in the brain. See Kreher et al., 2008 for more precise information, as the definition of edge probability used herein is based on the Probability Index of forming a part of the Bundle of Interest (PIBI) value concept developed by Kreher et al., 2008. The result of this step is one adjacency matrix per subject, that contains undirected weighted representations of edges, which correspond to a probability value that represents the chance that these specific anatomical connections really exist in a given patient.

Group Graph Reconstruction

In order to construct a meaningful group map one needs to identify the white matter connections (edges) which are shared by most individuals, the connectome backbone. A two-step strategy is preferably utilized to obtain that group connectome for the individual adjacency matrices containing anatomical connection probabilities. First each white matter adjacency matrix that was derived from probabilistic tracking based estimation of anatomical connectivity can be thresholded so that a sparsity of e.g. 20% is obtained. In such a process the single probabilities of anatomical connectivity are essentially sorted and a cut-off value of edge probability is applied, which cuts the total amount of edges admitted to the final adjacency matrix. With 20% sparsity we allow the top 20% of connections into the binary adjacency matrix for each individual. But that does not necessarily mean that the same approximately 1300 connections are written into the individual binarized adjacency matrices for each person, as the edge configuration (which nodes are connected by the edges admitted to the matrix) has no impact on the sparsity metric. Widely different connectivity patterns can theoretically have the same sparsity. Therefore in a second step the binary adjacency matrices of all participants can be added up, this way edges that were marked in the respective cell of the adjacency matrix by a number equal to the number of participants would be considered to be amongst the top 20% of edges for all of them. One can then apply a second thresholding process and identify those edges which are shared as the top 20% of most probable edges by all subjects (100%), 90% or 80% of the participants. Interestingly, the sparsity of such a group adjacency matrix containing edges that are shared by at least 90% of all participants lies around the widely reported (Gong et al., 2009a; Hagmann et al., 2007; Iturria-Medina et al., 2008) sparsity value of approximately 10%. It is important to mention, that there is no reason why this amount of edges (approximately 10% of all possible edges) is amongst the top 20% of edges with highest probability for all of the participants, if these are not the edges shared by 90% of the subjects. Converging lines of evidence suggest, that this value approximates the true number of edges in the human brain, when modeled as an undirected unweighted binary network with 116 nodes.

d) Determining a Weight for Each of the Edges Depending On the Centrality of the Respective Edge in the Connectivity Graph This relevance of a white matter fibre can be estimated from the anatomical links it provides within the white matter connectome (Sporns et al., 2005). A white matter connection linking central hub regions of the cortex that are not connected by any other fibre system are of highest relevance, while parallel connections that are one of many direct links between two regions are supposedly less critical to normal brain functioning (Achard et al., 2006). This form of local relevance, based on an analysis of the topology of the white matter network within which a structure is located, is expressed by the graph theoretical metric vulnerability (Rubinov and Sporns, 2009). High-vulnerability structures are located at points of the system (e.g. bottleneck structures) where the brain has low attack tolerance, points where destruction of that structure would affect the brain more majorly than a destruction at another point. As such it is not an absolute measure, but always relative to the topology of the considered network.

Processing of Individual Tractography Maps into Montreal-Neurological-Institute (MNI) or Brainlab Universal Atlas (BUA)-Space Group Maps Utilizing the same seed points as for the probabilistic tracking procedure as start mask we can perform additionally a deterministic streamline tracking and convert the resulting fibres into visitation maps in native DTI space. For all non-zero edges (e.g. A-B) in the binary group adjacency matrix—which we derived in the previous step from individual probabilistic estimations of anatomical connection probabilities—we can multiply voxel-by-voxel the binary visitation maps generated by the deterministic tracking from seeds of both nodes (e.g. visitation maps for fibres originating in A and visitation maps for fibres originating in B). The product of such a multiplication is a binary image containing non-zero values in those voxels which have been visited by fibres originating in both nodes, analogous to the probabilistic confluence maps but without the trajectory information on whether tracts are merging or connecting. Each confluence map was then smoothed using a gaussian kernel (3×3×3 voxels). These confluence maps for each edge were transformed into standard MNI/BUA group space by applying the normalization parameters estimated previously by normalizing the individual native space FA images into standard MNI/BUA space. The confluence maps from each participant and for each edge were finally averaged across participants so that group averaged confluence maps in group MNI/BUA space resulted for each edge.

e) Determining, for Each of the Edges, Which Voxels in a Dataset of the Brain of the Patient Belong to the Edges or are Passed by the Edges and Assigning or Adding the Determined Weight or the Respective Edges to All the Voxels Belonging to the Respective Edge to Obtain a Weighted Voxel-Based Dataset of the Brain of the Patient Defining the Vulnerability Field of the Brain By providing a method that allows us to back-project the mathematical properties we estimate from graph analysis of e.g. DTI reconstructed connectomes onto the brain, regions of the brain are weighted according to the underlying pattern of white matter connectivity. This is how anatomical regions such as the Precuneus (Gong et al., 2009a) are described as hubs or subpatterns such as motifs are identified (Iturria-Medina et al., 2008). The same approach of back-projecting mathematical graph properties of graph parts onto the corresponding brain regions may be used, but in the present case this is done for the edges instead of the nodes/vertices.

By analysing the back-projected properties, a voxel-by-voxel vulnerability map of cerebral white matter (i.e. white brain matter) can be generated that quantifies the vulnerabilty of each voxel on the basis to which graph edges it belongs to and which properties these edges have. A brain-wide map of voxel-wise vulnerability offers a tool to circumnavigate the most important parts of white matter during e.g. stereotactic surgery.

Voxel Vulnerability Weighting

The vulnerability metric for each edge in our group connectome (binary adjacency matrix containing edges that are shared by the group) is calculated and the non-zero voxels in the group averaged confluence map of each edge are multiplied with that vulnerability value. The resulting edge-specific vulnerability maps can then be summed up across edges, resulting in a final vulnerability sum map of cerebral white matter. The vulnerability metric describes how strongly the average shortest path lengths (the distance to get from any node A to any node B) in a network grow if an edge is removed. If an edge that exclusively connects otherwise unconnected regions is eliminated, regions are disconnected. Although this is practically never the case in the highly interconnected environment of the brain, some edges are more relevant than others, due to an insufficient amount of cost-effective (short) detours for reconnecting severed nodes.

f) Acquiring a Number of Potential Starting Points of the Trajectory

Preferably, at least one starting point of the trajectory to be planned is selected. More preferably, at least one potential starting point of the trajectory to be planned is acquired. More preferably, a number of, i.e. a plurality of, potential starting points are acquired. Each potential starting point advantageously lies in a target region which is defined as the target of the envisaged medical procedure, such as a surgical target or a radiation target which is to be irradiated with treatment radiation.

g) determining, for each of the number of starting points, at least one trajectory connecting the respective starting point with the target, the at least one trajectory passing through a number of respective adjacent voxels of the weighted voxel-based dataset This at least one trajectory connecting the respective starting point with the target is in particular an optimal trajectory which is determined as the trajectory having the shortest accessible path (in the case of neurosurgery taking into account the geometrical features of the probe in terms of diameter, rigidness etc.) leading from the target to the outer skull surface which primarily avoids organs at risk, in particular life-supporting structures (e.g. breathing and heartbeat-relevant brain stem nuclei and blood vessels in general), secondarily avoids the disruption of the neural main systems that connect the brain to the outer world and body (e.g. motoric: cortico-spinal tract, sensoric: optic tract, mixed: certain cranial nerves) and tertiarily avoids the disruption of brain function as far as possible. Such an automated calculation of trajectories is best suited for use in a stereotactic/keyhole surgery setup, since the trajectory can be estimated in this case directly on the basis of the used probe. But such vulnerability fields are of relevance for radiation therapy planning as well as they can incorporate radiation vulnerability estimates of certain locations in the brain (e.g. maximum allowed radiation dosage).

h) Adding the Weights of All Voxels Being Passed (i.e. Traversed) by the Respective Trajectory to Obtain a Respective Weighted Trajectory On that basis an inverse planning procedure is preferably implemented, where the optimal (rigid, bowed or with multiple angles—depending on the probe utilized) surgical trajectory or a set of radiation trajectories (i.e. directions in which ionizing radiation is to be applied for radiation treatment) can objectively be estimated on the basis of the three-dimensional vulnerability field superimposed on the surgical target area in question (or the entire brain). The trajectory to be used for the envisaged medical procedure is the trajectory which is associated with the lowest medical risk and therefore has the in particular lowest vulnerability weighting $VUL(x, y)$.

For each of these factors one specific vulnerability map can be generated, and these maps can contain a mixture of qualitative and quantitative information.

In summary information-specific layers are generated that contain ratings (nominal scale: avoid/go, ordinal scale: vulnerability/attack resilience ratings of voxels, full metric: brain function disruption score) for each specific voxel. Information layers are generated automatically but can be modified by the user. The information layers are then combined into one final vulnerability map (again the weighting/how the information layers are to be combined can be adjusted by the user but has a preset/default configuration) on the basis of which the optimal surgical trajectory to a given target is calculated (semi-)automatically.

More specifically, this invention concerns not only the combination framework for the specific information layers but explicit workflows and procedures for the individualized generation of such information layers (specifically for the analysis of the individual white matter network).

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The invention also relates to a medical diagnostic system comprising at least a medical imaging device for generating the medical image data on which the nerve-indicating dataset can be based, and the aforementioned computer for processing in particular the medical image data. The medical imaging device comprises (in particular is) for example an x-ray device, a CT or MR scanner or an ultrasound imaging device. The medical imaging device preferably is operatively coupled to the computer for transmission of signals and in particular the data which is processed during execution of the disclosed method.

Definitions

In this section, definitions for specific terminology used in this disclosure are offered which also form part of the present disclosure.

Vulnerability Information Layer

A vulnerability information layer is understood to be a three dimensional voxel image that contains intensities which are directly proportional to the disruption to health or brain function if that voxel in question is to be destroyed or in any other detrimental way modified (e.g. due to radiation therapy). Possible examples are:

a grey matter tissue segmentation map—if marked voxels are destroyed neural mass is lost, destruction/resection of tissue in high intensity voxels will disrupt brain function more severely than destruction/resection of tissue in low intensity voxels (no neural mass affected)
- a functional map marking voxels belonging to a specific functional brain network (e.g. sensorimotor functional connectivity system—enclosing voxels in the primary motor cortices and the midline supplementary motor area) originating from functional connectivity analysis of resting state or task-dependent functional Magnetic Resonance Imaging time series—if marked voxels are destroyed sensori-motor functions are interrupted, destruction/resection of tissue in high intensity voxels will disrupt sensorimotor function more severely than destruction/resection of tissue in low intensity voxels
- a probabilistic map derived from navigated Transcranial Magnetic Stimulation (TMS) of e.g. language function related brain sites containing voxels that are marked based on TMS induced speech disruption, the voxel intensities correspond to a probability for this voxel to belong to a speech relevant brain system—if marked voxels are destroyed speech abilities are likely to be impaired, destruction/resection of tissue in high intensity voxels will disrupt language functions more severely than destruction/resection of tissue in low intensity voxels
- an Arterial Spin Labelling based perfusion map containing regional Cerebral Blood Flow values, destruction/resection of tissue in high intensity voxels will disrupt cerebral perfusion more severely than destruction/resection of tissue in low intensity voxels and might coincide with an increased risk of cerebral haemorrhage
- a metainformation map generated in an evidence-based manner directly from scientific literature or clinical databases containing maximum radiation exposure values for each voxel, such a map can be inverted by a weighting so that voxels with the highest vulnerability value are voxels with lowest radiation tolerance and voxels with the lowest vulnerability value are voxels with the highest radiation robustness It is important to note that such images are not restricted to contain intensity information in a three-dimensional slice set, local vulnerability can change over time (during a surgical intervention), therefore in one embodiment vulnerability information layers are four-dimensional objects, with the fourth dimension considering the changing vulnerability field over time and allowing more precise/adaptive planning.

Weight Information Layer

Two types of vulnerability information layers or products of previous information layer/weighting layer multiplications are linked by voxel-specific weights which are stored in a three-dimensional voxel space that is in alignment with the vulnerability information layers it is supposed to link. Such weighting layers can contain the same value in all voxels or have locally specific voxel-specific values. Possible examples are:
- the combination of a grey matter vulnerability map and a white matter vulnerability map is exclusive as the two tissue types are generally not in overlap, the weighting layer is W(x,y,z)=1, for both grey and white matter vulnerability images
    Combined_vulnerability(x,y,z)=White_Matter(x,y,z)*W(x,y,z)+Grey_Matter(x,y,z)*W(x,y,z)
    The resulting image (Combined_vulnerability) contains voxel-specific values, informing of the locations of white and grey matter which are to be avoided
- The combination of a grey matter map and a perfusion map contains regions that naturally overlap, we wish to accentuate in our final vulnerability map strongly perfused grey matter regions over other perfused tissue types, the weighting layer for the grey matter map contains at all voxels where the grey matter map is non-zero e.g. a weight of 10 (WG), while the perfusion map is accentuated for high perfusion regions (all weights WP in locations with a cerebral perfusion >80 ml/100 g/min are set to 2 all other weights are set to one)
    Combined_vulnerability(x,y,z)=Perfusion_image(x,y,z)*WP(x,y,z)+Grey_Matter(x,y,z)*WG(x,y,z)
    The resulting image (Combined_vulnerability) contains voxel-specific values, which inform the trajectory finding algorithms about how to avoid highly perfused zones in general, and more specifically highly perfused grey matter zones
- A modification weight information layer containing conditional probabilities which are based on medical evidence that modify the vulnerability information layer on the basis of patient-specific characteristics, e.g.
    The patient belongs to a certain category in terms of age, gender and blood pressure which increases the probability of a surgery induced cerebral bleeding in certain locations, the patient specific information is utilized to modify the vulnerability information layer accordingly without necessarily explicitly altering how it is to be combined with other information layers.

Vulnerability Information Layer Generation:

The vulnerability information layers can be generated from at least one of atlas information (also called atlas-based information), population-based information or the scientific literature. Alternatively or additionally, the vulnerability information layers can be generated based on applying one of the imaging modalities mentioned above with regard to step a) for generating patient-specific image data, in particular by application of PET, T1-MR, fMRI CT- or MR-based angiogram, pASL, ASL, Doppler imaging, DTI, DSI, q-Ball or HARDI.

In one embodiment the system has a predefined set of vulnerability-information layer images that have been generated offline and prior to loading the patient data based on the scientific literature and available atlases. These are a default set of information-layers that are to serve with information in case there is no patient specific data available (e.g. if no perfusion imaging has been/can be conducted with a patient, the use of a population-based perfusion map in the planning process is superior to not using such a map at all). All such population-based non-patient-specific vulnerability-information layer images, voxel-specific weighting fields or atlases have not been acquired/generated in the patient specific image space, and therefore have to be co-registered (preferably utilizing an elastic fusion process) into the individual patient image space, prior to the planning step.

Utilizing an elastic fusion process to obtain overlap of the individual patient images and voxel-by-voxel weighting information and vulnerability-information layers allows for the combination of population-validated input on optimal trajectories in case no patient-specific information is available. The combination of generating vulnerability-information layers and weighting information layers in the patients individual voxel-space as well as bringing predefined or preprocessed layers of such information into the individual patient space for the purpose of optimized quantitative surgical/radiation trajectory planning is an essential step in this workflow.

Examples of atlas-based information are the demarcation of significant sub-cortical or cortical grey matter structures, delineation of major white matter tracts (e.g. cortico-spinal tract, cranial nerves) or known vessel structures.

Examples of scientific literature based information-layers are voxel-by-voxel demarcations of known high-importance brain regions (brain connectivity hubs), known descriptions of points (landmarks/zones) known to be more at risk to cause problems during (neuro-)surgical or radiation procedures (e.g. specific vessel tree high-pressure points, locations of increased cranial bleeding known from the neurosurgical literature etc.).

In one embodiment such prior maps which are non-specific to the patient at hand are generated bottom-up from large amounts of available patient data (in cloud computing or other settings), atlases or by repeatedly parsing scientific literature and are continuously (semi-) automatically improved with the growing data basis and improved analytic algorithms. In such an embodiment the automated validity check prior to an integration into the relevant information layers and automatic methods for collating such data are of highest significance, that information amounts that are unprocessable to a single individual are integrated in a reliable fashion. As such, automated checking procedures for the validity and safety of such an information-layer update (comparing new predicted damage with earlier predicted damage).

Computer Program etc.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). A computer herein is a technical computer which comprises in particular technical, in particular tangible components, in particular mechanical and/or electronic components. Any device mentioned herein is a technical, in particular tangible device.

Imaging Methods (Imaging Modalities)

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, in particular volumetric CBCT), x-ray tomography, magnetic resonance tomography (MRT or MRI), conventional x-ray, sonography and/or ultrasound examinations, and positron emission tomography. Analytical devices in particular are used to generate the image data in apparatus-based imaging methods. The imaging methods are in particular used for medical diagnostics, to analyse the anatomical body in order to generate images which are described by the image data. The imaging methods are also in particular used to detect anatomical structures or pathological changes in the human body. Imaging methods are in the framework of this disclosure also called medical imaging methods, imaging modalities and/or medical imaging modalities.

Data Processing Method

The method in accordance with the invention is in particular a data processing method. The data processing method is preferably performed using technical means, in particular a computer. The data processing method is preferably constituted to be executed by or on a computer, in particular it is executed by or on the computer. I particular, all the steps or merely some of the steps (i.e. less than the total number of steps) of the method in accordance with the invention can be executed by a computer. The computer in particular comprises a processor and a memory in order to process the data, in particular electronically and/or optically. The calculating steps described are in particular performed by a computer. Determining steps or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term "computer" includes a cloud computer, in particular a cloud server. The term "cloud computer" includes a cloud computer system which in particular comprises a system of at least one cloud computer and in particular a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. In particular, the term "cloud" is used in this respect as a metaphor for the Internet (world wide web). In particular, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals in particular represent the data received or outputted by the computer. The computer is preferably operatively coupled to a display device which allows to display information outputted by the computer e.g. to a user. An example of a display device is an augmented reality device (also called augmented reality glasses) which may be used as goggles for navigating. A specific example of such augmented reality glasses is Google Glass (trademark of Google Inc.). An augmented reality device may be used to both input information into the computer by user interaction and to display information outputted by that computer.

Acquiring Data

The expression "acquiring data" in particular encompasses (within the framework of a data processing method) the scenario in which the data are determined by the data processing method or program. Determining data in particular encompasses measuring physical quantities and transforming the measured values into data, in particular digital data, and/or computing the data by means of a computer and in particular within the framework of the method in accordance with the invention. The meaning of "acquiring data" also in particular encompasses the scenario in which the data are received or retrieved by the data processing method or program, for example from another program, a previous method step or a data storage medium, in particular for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, in particular determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image Fusion (Elastic Fusion)

Image fusion can be elastic image fusion or rigid image fusion. In the present invention, it is preferred that image fusion is conducted by applying rigid fusion. In case of rigid image fusion the relative position between the pixels or voxels of an image (2D or 3D) is fixed while in case elastic image fusion, the relative positions are allowed to change.

In this application, the term "image morphing" is also used as an alternative to the term "elastic image fusion", but with the same meaning Elastic fusion transformations (for example, elastic image fusion transformations) are in particular designed to enable a seamless transition from one data set (for example a first data set such as for example a first image) to another data set (for example a second data set such as for example a second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). These constraints include in particular the constraint that the transformation is regular, which in particular means that a Jacobian determinant calculated from a matrix of the deformation field (in particular, the vector field) is larger than zero, and the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or generic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $1/10$ or $1/100$ or $1/1000$ of the diameter of the image, and in particular about equal to or less than the distance between neighbouring voxels. Large deformations can be implemented, in particular due to a high number of (iteration) steps.

The determined elastic fusion transformation can in particular be used to determine a degree of similarity (or similarity measure, see above) between the first and second data sets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can in particular be determined on the basis of a determined correlation between the first and second data sets.

DESCRIPTION OF THE FIGURES

In the following, an example embodiment will be described by reference to the Figures, wherein the invention shall not be limited to the features described in connection with the Figures, and wherein

FIG. 5 shows a representation of a real fibre bundle;

FIG. 6 shows the principle of generating a confluence map; and

FIG. 1 is an illustration of the information layer combination principle for a 2D-pixel-images case, the number of information layers A, B, C is arbitrary, additional layers can be added by the user (by acquiring additional modalities or drawing objects or fields of his/her choice) and weighted accordingly. The weighting fields can be modality specific (all voxels weighed with one coefficient) or voxel-specific (each voxel has a specific weight in a modality, e.g. due to atlas-based prior knowledge.

FIG. 2 shows a workflow for generating a vulnerability field from medical image data acquired by application of a plurality of medical imaging modalities. Each one of the imaging modalities has different imaging capabilities depending on e.g. the type of tissue which may be imaged with the respective imaging modality. Thus, combination of different of information layers generated with different imaging modalities may serve to generate a vulnerability field which comprises information about different kinds of medical risks which depend on e.g. the tissue type which can be imaged by the respective imaging modality. Images of patient X are acquired prior to surgery/radiotherapy and co-registered into one patient-specific space, vulnerability information is extracted from each modality, then optionally verified and adjusted by the user and finally combined in the next step. If images from one modality are not available, appropriate vulnerability information layers A, B, C for that missing modality (D) can be loaded from appropriate population/sample-based data or such that are based on earlier scans of the patient X in question (intraoperative case where not all modalities can be acquired or images do not have the same quality as preoperative recordings).

Figure 1:
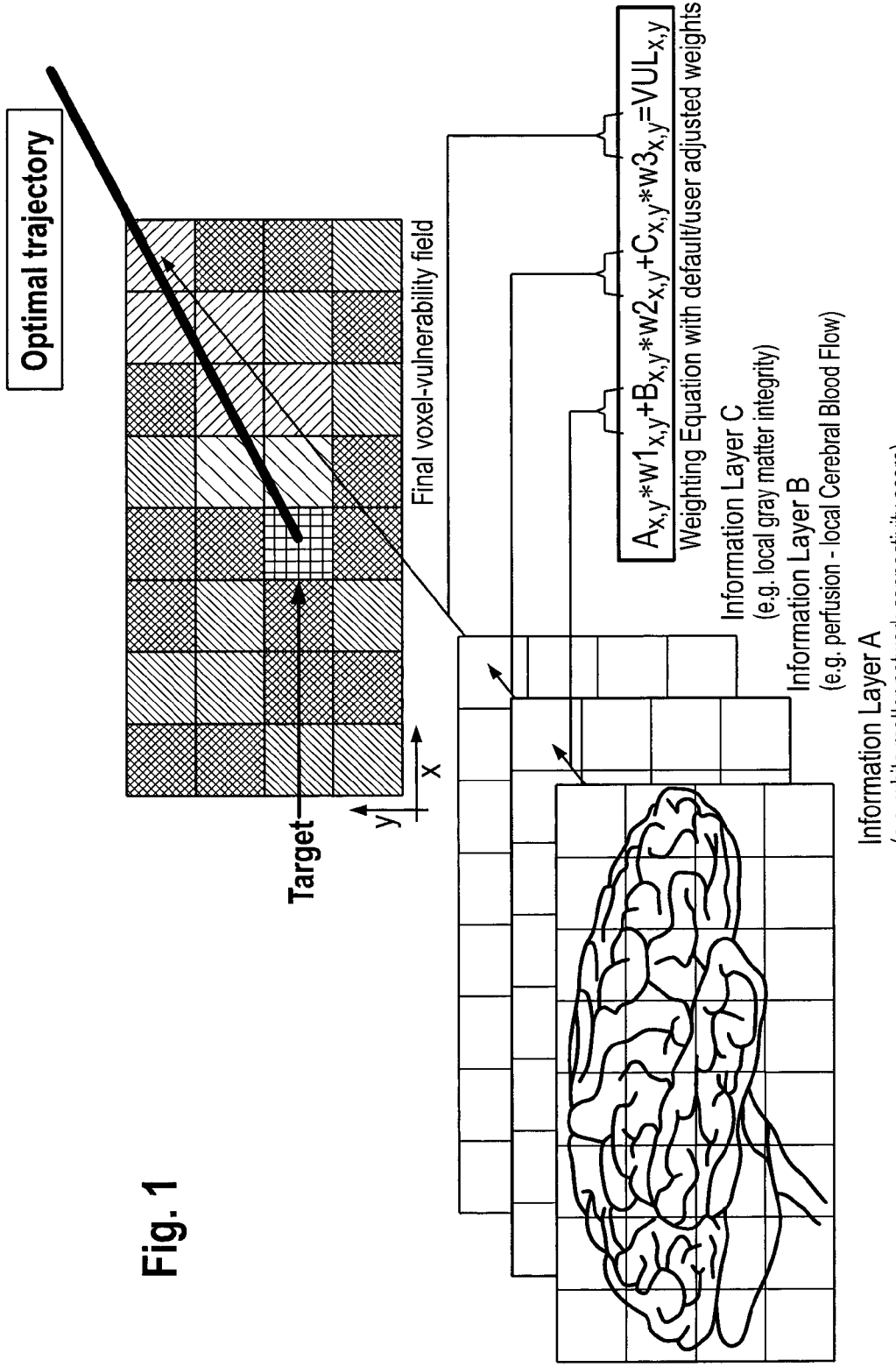
FIG. 1 is an illustration of the information layer combination principle.
Figure 2:
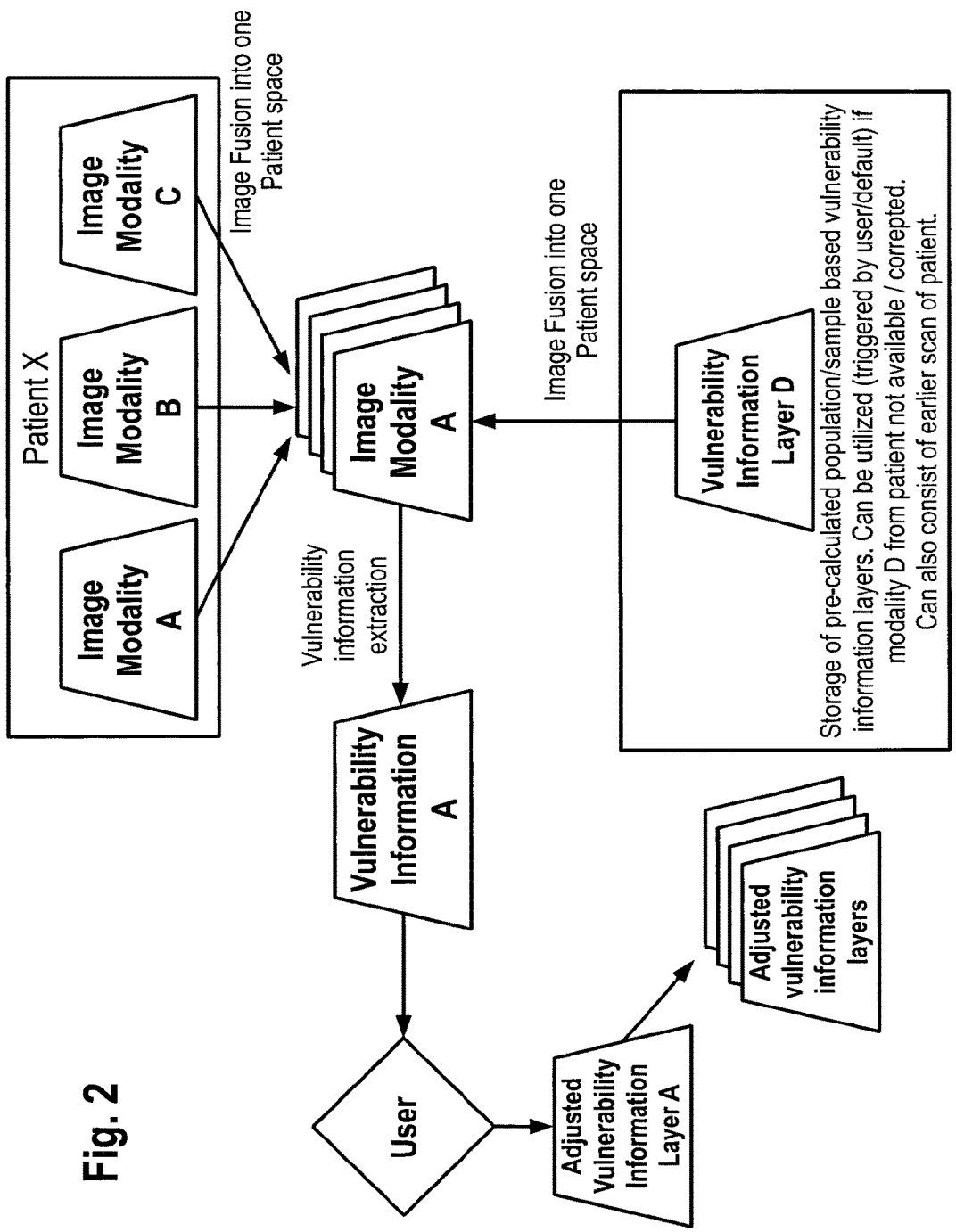
FIG. 2 shows a workflow for generating a vulnerability field.
Figure 3:
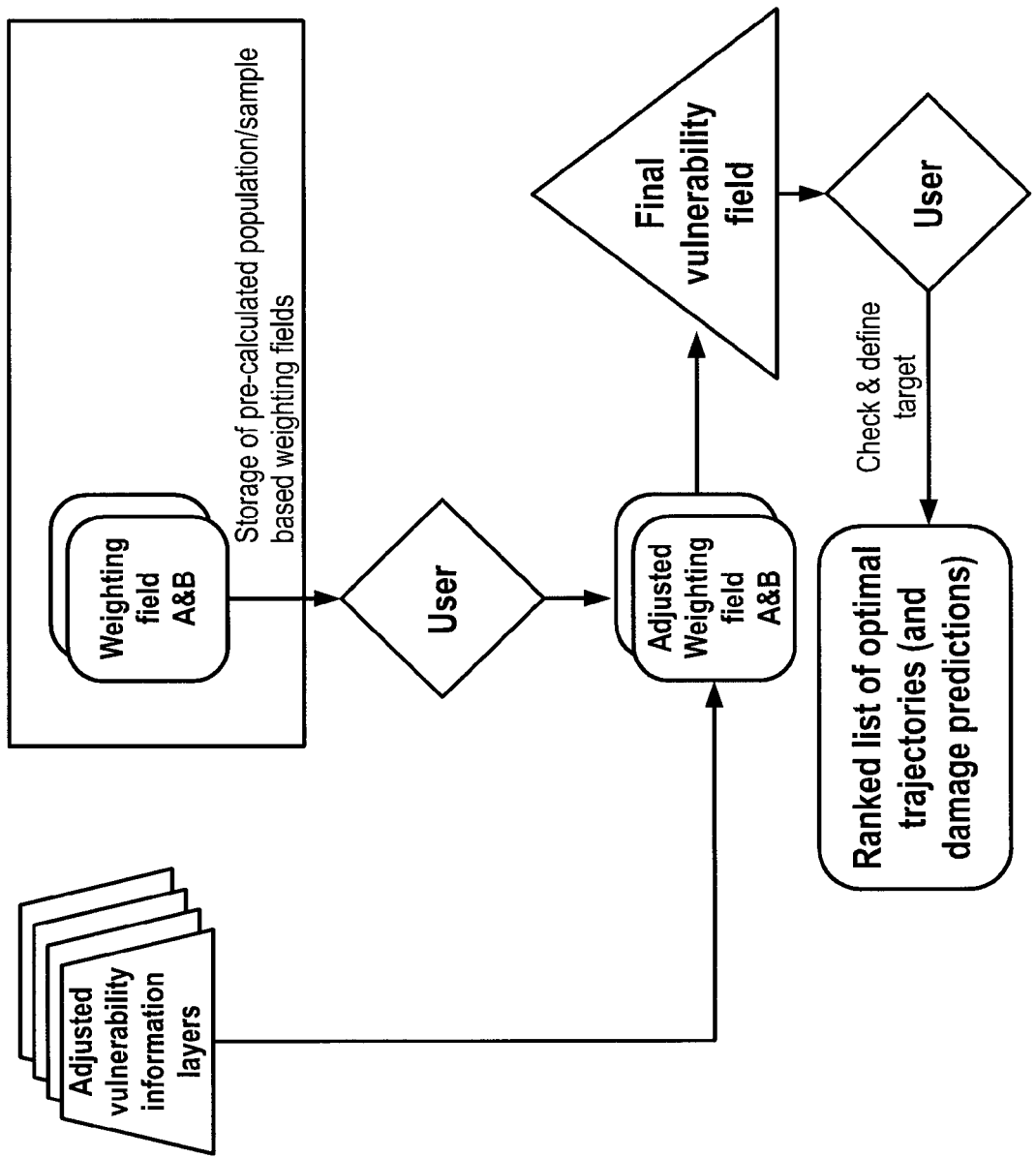
FIG. 3 shows a workflow for generating a ranked list of trajectories.

According to FIG. 3, the adjusted vulnerability information layers are combined based on a default or user adjusted combination scheme, for this combination scheme (essentially the voxel-by-voxel equation utilized to calculate the final vulnerability field) weighting fields can be loaded from previously stored databanks (which again can be optionally modified, adjusted and verified by the user). The final vulnerability field is generated from the adjusted vulnerability information layers and the corresponding weighting fields. The user has defined the surgical/radiotherapy target and receives a ranked list of optimal trajectories (trajectories that have a minimal physiological cost based on the final vulnerability field). The user then chooses the trajectory or accepts the default optimal trajectory.

Figure 4:
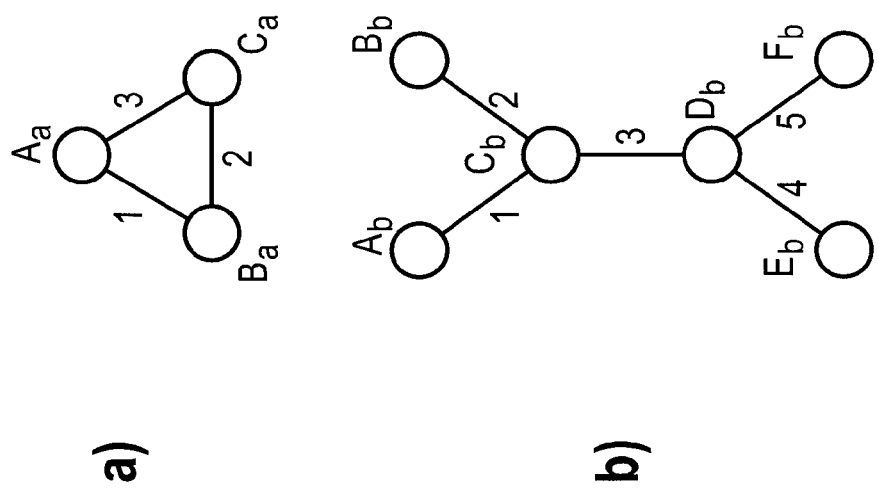
FIG. 4 shows two cases of edge vulnerability.

FIG. 4 illustrates two cases a) and b) of edge-vulnerability, disconnecting the upper graph at any edge is equivalent, disconnecting the lower graph at edge 3 is more dramatic than a disconnection at another site. In both cases a), and b), edges 1, 2, 3, 4, 5 connect nodes $A_a$, $B_a$, $C_a$, and $A_b$, $B_b$, $C_b$, $D_b$, $E_b$, $F_b$, respectively. FIG. 5 illustrates an edge 1 representing a real fibre bundle connection between two hypothetical cortical zones A & B of the brain 6 and the node-edge-graph representation.

FIG. 6 illustrates the principle for the generation of a population-base and/or sample-based confluence map for the identification of the physical location of the voxel corresponding to a given edge of the brain anatomical connectivity graph. In this example, the confluence map is generated from DTI image data and allows to determine the location of an edge 1 representing a fibre bundle.

Figure 7:
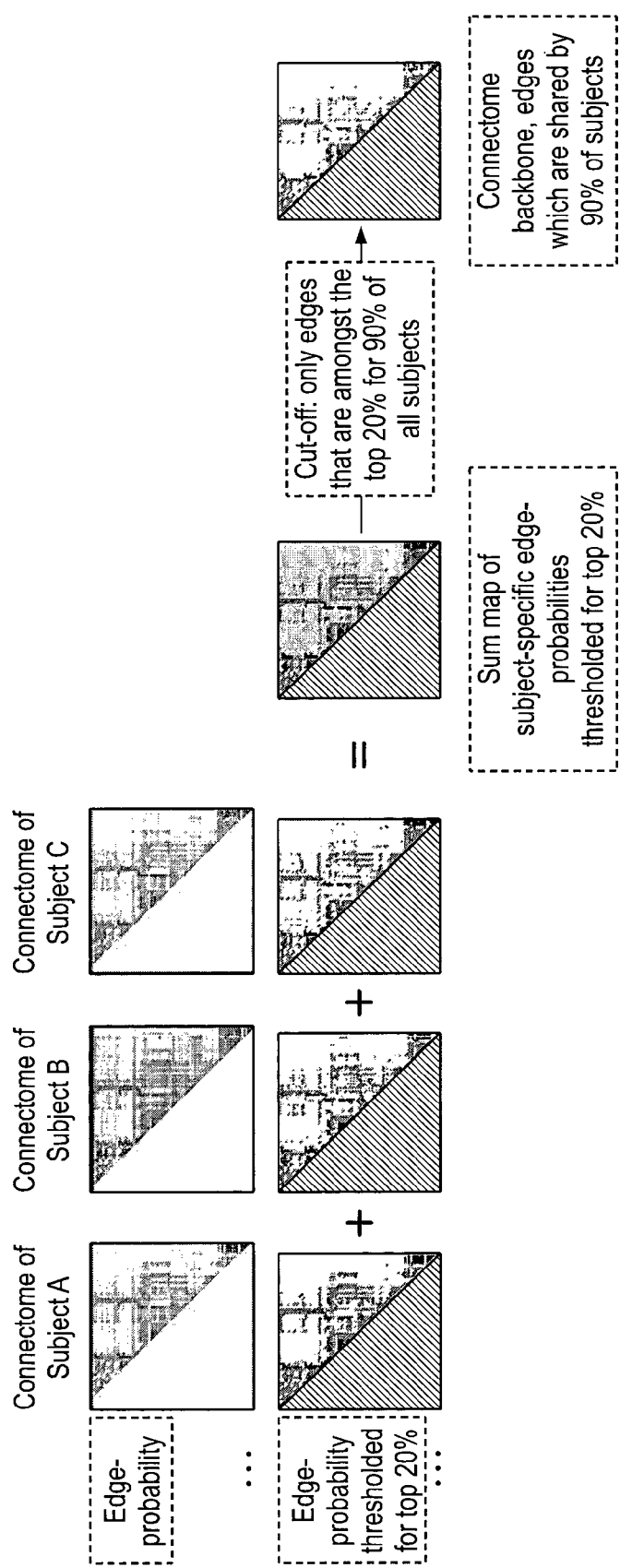
FIG. 7 shows the principle of generating a connectome-backbone.

FIG. 7 illustrates the principle of generating a connectome-backbone for a population or sample from individual connectivity adjacency matrices. Description relating to FIG. 7 is also provided above in the section "Group graph reconstruction".

The invention claimed is:

1. A medical system, comprising:
a medical imaging device for generating medical image data utilized for generating a nerve-indicating dataset comprising information about a brain of a patient suitable for identifying neural fibres in the brain of the patient;
at least one computer operably coupled to the medical imaging device and having at least one processor and memory with instructions, the instructions, when executed on the computer, configuring the computer to determine a weight of a trajectory between a starting point and a target within the brain of the patient using a vulnerability field of the brain, by:
acquiring, at the at least one processor, the medical image data and determining, by the at least one processor and based on the medical image data, the nerve-indicating dataset;
determining, by the at least one processor, a plurality of nodes within the brain;
determining, by the at least one processor, axonal linkage of the nodes based on the nerve-indicating dataset to obtain edges connecting the nodes, the nodes and edges constituting a connectivity graph;
determining, by the at least one processor, a weight for each of the edges depending on a statistical measure of the respective edge in the connectivity graph;
determining, by the at least one processor and for each of the edges, which of a plurality of voxels in a dataset of the brain of the patient belong to the edges or are passed by the edges and assigning, by the at least one processor, or adding, by the at least one processor, the determined weight of the respective edges to all of the voxels belonging to the respective edge to obtain a weighted voxel-based dataset of the brain of the patient defining the vulnerability field of the brain;
acquiring, at the at least one processor, a number of potential starting points of at least one trajectory between each of the starting points and a target in the brain;
determining, by the at least one processor, and for each of the starting points, the at least one trajectory connecting the respective starting point with the target, the at least one trajectory passing through a number of respective adjacent voxels of the weighted voxel-based dataset;
adding, by the at least one processor, the weights of all voxels being passed by the respective trajectory to obtain a respective weighted trajectory.

2. A method for determining a weight of a trajectory between a starting point and a target within a brain of a patient using a vulnerability field of the brain, the method comprising executing, by at least one processor of at least one computer, the steps of:
acquiring, at the at least one processor, a nerve-indicating dataset comprising information about the brain of the patient suitable for identifying neural fibres in the brain of the patient;
determining, by the at least one processor, nodes within the brain;
determining, by the at least one processor, the axonal linkage of the nodes based on the nerve-indicating dataset to obtain edges connecting the nodes, the nodes and edges constituting a connectivity graph;
determining, by the at least one processor, a weight for each of the edges depending on a measure of the respective edge in the connectivity graph;
determining, by the at least one processor, for each of the edges, which voxels in a dataset of the brain of the patient belong to the edges or are passed by the edges and
assigning, by the at least one processor, or adding, by the at least one processor, the determined weight of the respective edges to all of the voxels belonging to the respective edge to obtain a weighted voxel-based dataset of the brain of the patient defining the vulnerability field of the brain;
acquiring, by the at least one processor, a number of potential starting points of a trajectory;
determining, by the at least one processor and for each of the number of starting points, at least one trajectory connecting the respective starting point with the target, the at least one trajectory passing through a number of respective adjacent voxels of the weighted voxel-based dataset;
adding, by the at least one processor, the weights of all voxels being passed by the respective trajectory to obtain a respective weighted trajectory.

3. The method of claim 2, wherein the weight for each of the edges depends on a graph statistical measure of the respective edges in the connectivity graph.

4. The method of claim 2, wherein step b) of determining nodes within the brain includes the steps of:
acquiring, at the at least one processor, an atlas dataset representing an atlas of the brain defining the positions of nodes within the brain;
calculating, by the at least one processor, a matched atlas dataset by registering the atlas dataset with the nerve-indicating dataset, the matched atlas dataset defining the positions of the nodes within the brain of the patient.

5. The method of claim 2, wherein determining nodes within the brain includes a step of determining the nodes by the at least one processor and based on the nerve-indicating dataset or another nerve-indicating dataset of the brain of the patient.

6. The method according to claim 2, wherein the weighted trajectory is determined, by the at least one processor, as the trajectory to be used in a medical procedure based on its weighting.

7. The method according to claim 2, wherein the potential starting points are located in a target region of an envisaged medical procedure.

8. The method according to claim 7, wherein the nerve-indicating dataset is acquired by the at least one processor, from image data which was generated by applying a medical imaging modality, of at least one of diffusion tensor imaging, magnetic resonance imaging, positron emission tomography, computed tomography imaging, ASL, and Doppler imaging.

9. The method according to claim 2, wherein the weighted trajectory is determined, by the at least one processor, to be an optimal trajectory for avoiding organs at risk.

10. The method according to claim 2, wherein the centrality of the respective edge in the connectivity graph represents a measure for the importance of the connection of the nodes by that edge, a measure for the probability that there is another path for connecting those nodes.

11. The method according to claim 2, wherein the connectivity graph represents a bundle of white brain matter fibres.

12. The method according to claim 2, further comprising determining, by the at least one processor and based on the determined vulnerability field, the probability of disconnecting a functional region of the brain if a specific one of the edges is removed.

13. The method according to claim 2, wherein the vulnerability field is determined as a combination of a plurality information layers, each information layer describing a different type of risk.

14. The method according to claim 13, wherein each information layer is determined by the at least one processor and based on medical image data acquired with each a different medical imaging modality.

15. The method according to claim 13, wherein the weights of all voxels are added, by the at least one processor as a linear combination of all voxels in all vulnerability fields which are passed by the respective trajectory.

16. A computer program product comprising a non-transitory computer usable medium including a computer readable program wherein the computer readable program, when executed on a computer, causes the computer to determine a weight of a trajectory between a starting point and a target within a brain of a patient using a vulnerability field of the brain, the computer readable program further causing the computer to:
  acquire, at the at least one processor, a nerve-indicating dataset comprising information about the brain of the patient suitable for identifying neural fibres in the brain of the patient;
  determine, by the at least one processor, nodes within the brain;
  determine, by the at least one processor, the axonal linkage of the nodes based on the nerve-indicating dataset to obtain edges connecting the nodes, the nodes and edges constituting a connectivity graph;
  determine, by the at least one processor, a weight for each of the edges depending on a graph theoretical statistical measure of the respective edge in the connectivity graph;
  determine, by the at least one processor, for each of the edges, which voxels in a dataset of the brain of the patient belong to the edges or are passed by the edges and assigning, by the at least one processor, or adding, by the at least one processor, the determined weight of the respective edges to all of the voxels belonging to the respective edge to obtain a weighted voxel-based dataset of the brain of the patient defining the vulnerability field of the brain;
  acquire, by the at least one processor, a number of potential starting points of at least one trajectory connecting each of the respective starting points with a target in the brain;
  determine, by the at least one processor and for each of the number of potential starting points, at least one trajectory passing through a number of respective adjacent voxels of the weighted voxel-based dataset;
  add, by the at least one processor, the weights of all voxels being passed by the respective trajectory to obtain a respective weighted trajectory.

* * * * *